US00PP13077P2

(12) United States Plant Patent
Fontanazza

(10) Patent No.: US PP13,077 P2
(45) Date of Patent: Oct. 15, 2002

(54) OLIVE TREE 'DON CARLO'

(75) Inventor: Giuseppe Fontanazza, Perugia (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 0 days.

(21) Appl. No.: 09/670,008

(22) Filed: Sep. 25, 2000

(51) Int. Cl.[7] ..... A01H 5/00

(52) U.S. Cl. ..... Plt./158

(58) Field of Search ..... Plt./158

(56) References Cited

PUBLICATIONS

UPOV–ROM GTITM Computer Database 2000/01, Feb. 6, 2001, GTI Jouve Retrieval Software, Citation for 'Don Carlo'.*

* cited by examiner

*Primary Examiner*—Bruce R. Campell
*Assistant Examiner*—Annette H. Para
(74) *Attorney, Agent, or Firm*—Morrison & Foerster L.L.P.

(57) ABSTRACT

The present invention comprises a new and distinct selection of *Olea europaea L.* (popularly known as the olive tree) hereinafter referred to as *Olea europaea* cultivar Don Carlo. *Olea europaea* cultivar Don Carlo exhibits medium plant vigor, erect on average branch structure, greyish green fruit and superior olive oil.

4 Drawing Sheets

BACKGROUND OF THE INVENTION

Olive oil continues to increase in popularity. There is a continuing need to develop new and improved olive oils to meet the increased demand for use in various food types and in cooking. As a result, there is a need for the development of new olive cultivars which produce oils yielding superior quality olive oil.

BRIEF SUMMARY OF THE INVENTION

In order to meet these needs, the present invention is directed to a new olive cultivar named *Olea europaea* cultivar 'Don Carlo'. The olive cultivar of this invention was obtained by means of mass-selection on a seed population of the Frantoio cultivar derived from self pollination. The plant exhibits medium plant vigor, erect on average branch structure and greyish green fruiting branches. The bark color is greyed-green (code 191/A, according to R.H.S. Colour Chart), upper side foliage colour is greyed-green (code 195/A, according to R.H.S. Colour Chart), lower side foliage colour is greyed-green (code 195/C, according to R.H.S. Colour Chart), opened flower is yellow-green (code 150/D, according to R.H.S. Colour Chart), flower bud color is yellow-green (code 145/C, according to R.H.S. Colour Chart), and seed colour (endocarp) is grey-brown (code 199/D, according to R.H.S. Colour Chart). 'Don Carlo' has been asexually reproduced by self-rooting a cutting branch in Garda and Molise, Italy. The plants as asexually reproduced remain true to type.

BRIEF DESCRIPTION OF THE DRAWINGS

FIG. 1 is a photograph of a specimen of the new variety exhibiting its overall appearance.

FIG. 2 is a photograph of a typical branch of the new variety bearing fruit.

FIG. 3 is a photograph of a typical branch of the new variety bearing fruit; the leaves of the new variety showing the upper side (two left leaves) and lower side (two right leaves) of the leaves; the fruit of the new variety; a cross section of the fruit of the new variety and the seeds of the new variety.

FIG. 4 is a photograph of the inflorescences of the new variety.

DESCRIPTION OF THE INVENTION

The present invention concerns an olive variety of medium vigour and generally having an erect branch structure.

According to the International Code of Botanical Nomenclature, the cultivar name chosen is *Olea europaea L.* cv 'Don Carlo'.

The present variety has been obtained by means of the mass-selection used, for about 20 years, with a large *Olea europaea L.* seed population, deriving from embryos obtained by self-pollination of the cultivar Frantoio. Initially subjects with a high rooting aptitude were individually selected and subsequently the vigour of the studied subjects were verifed selecting those having more moderate vigour, once the growth stage was behind the selection regarded the genotypes bearing larger fruit size. Within these, the new genetic line, object of the present description—from the point of view of the average character of the fruit and from its self-pollinating properties, was chosen. The present variety clearly distinguishes itself from all the other known varieties and has homogeneous and stable characteristics. For the constitution of the present variety, the objective was to overcome the self-sterility problem, which recurs in the olive and which in the specific case is accompanied by elevated rooting attitude, early production stage, high productivity, high oil yield. The new genotype gives late ripening, attitude to mechanical harvesting, resistance to cold and to the most common parasites of the olive.

The response of the present variety has been studied through observations repeated for years and in different environments (for about 13 years) in the olive growing areas of Garda and Molise. On the basis of the results, it was possible to ascertain that the present variety possesses excellent agronomic, biological and technological characteristics, which makes this variety one of great value. The resulting plants show an excellent growth both in the nursery and in the field, having moreover, the peculiarity starting from the third year of forming very few sterile branches as the new growths show productive properties.

The distinctive characteristics of this variety are reported in the following description. The described plant was 10 years of age and grown with or without irrigation with 5'×3' spacing.

Four photographs are attached to the present description of the varieties showing the entire plant, fruiting branches, a series of inflorescences and one showing a fruit bearing branch, leaves, entire and sectioned drupes and stones.

DETAILED BOTANICAL DESCRIPTION

CY DON CARLO

Plant:

*Vigour*.—Medium.
*Attitude*.—Erect.
*Crown density*.—Medium.
*Abnormal leaves*.—Absent.

The size and shape of olive trees when mature essentially depends upon the kind of pruning and spacing used. If the plant is trained as central leader (monocono-shape), it is possible to control the height of the plant to between about 3.5 meters and about 4 meters and the diameter of the canopy to about 2.6 meters. When the trees are freely grown, the size and the shape assumed by the plants are typical of species *Olea europaea L.* In addition, the wood texture and color are typical of species *Olea europaea L.*

Branches and drupes:

*Color*.—Grey-green.
*Internodes*.—Short.
*Feathers*.—Generally present.

The branch size essentially depends upon the age of the branch observed. The crotch angle of a one year old branch typically ranges from about 45 degrees to about 85 degrees, as measured from the longitudinal axes of the plant.

Leaf

*Dimension*.—Medium.
*Longitudinal dimension*.—From 73 mm to 75 mm.
*Transversal dimension*.—13 mm to 15 mm.
*Axis ratio* (*length/width*).—Short and large (about 5.5).
*Shape*.—Elliptical-lanceolate.
*Leaf glossiness*.—Absent.
*Upper side color*.—Dark-green.
*Longitudinal axis curvature of the blade*.—Flat.
*Twisting*.—Present.

The leaf apex is rounded with slight swaging and twisting, and the leaf base is sharp. The arrangement of the leaves is typical of species *Olea europaea L.* (two opposite leaves per each node). The leaf surface is glabrous and flat. The upper side color of the leaf is green (code 139/A, according to R.H.S. Colour Chart), and the lower side color of the leaf is greyed-green (code 195/A, according to R.H.S. Colour Chart).

Inflorescence:

*Shape*.—Particulate spike-shaped.
*Structure*.—Short and compact.
*Ramification*.—Medium.
*Axillary flowers*.—Absent.
*Average number of flowers per inflorescence*.—15–18.

Flower:

*Dimensions of the floral bud*.—Medium.

Reproductive organs (stamen and pistil), as well as the rest of the flower (petals and sepals) have the typical size, number, shape, and color as species *Olea europaea L.* For instance, the inflorescence is a cluster (15–18 flowers per cluster), the number of sepals is four, and the number of petals is four. The percentage of ovary abortion is very low (less than about 5%) and the percentage of pollen viability is between about 95% and about 98% when the plant is at optimal nutrition.

Fruit (drupe): In the following description, position A refers to the position in which the fruit shows its largest asymmetry. Position B can be reached from position A by turning 90° along the longitudinal axes in a way that presents the most developed part of the fruit to the observer (according to UPOV rules).

*Dimension*.—Medium.
*Shape*.—Elliptical.
*Colour*.—Dark violet.
*Pigmentation*.—Medium.
*Symmetry A*.—Slightly asymmetrical.
*Symmetry B*.—Symmetrical.
*Position of the maximum diameter*.—Central.
*Apical shape in A position*.—Rounded.
*Apical shape in B position*.—Rounded.
*Mucron*.—Present.
*Pistil scar position*.—Central.
*Base shape in A position*.—Truncated.
*Base shape in B position*.—Truncated.
*Penduncular cavity width*.—Narrow.
*Penducular cavity shape*.—Circular.
*Pendicular cavity depth*.—Medium.
*Transversal section shape*.—Circular.
*Oil content*.—About 18% to about 21% (fresh matter based).

The apex of the fruit is rounded, with mucron present, and the base of the fruit is truncated. The dimensions of the fruit range from about 3.5 to about 5.0 g, with longitudinal diameter from about 18 mm to about 22.5 mm and transversal diameter from about 12.5 mm to about 15 mm, depending on the yield of the plant.

Stone (endocarp):

*Shape in A position*.—Elliptical.
*Shape in B position*.—Elliptical.
*Symmetry in A position*.—Slightly asymmetrical.
*Symmetry in B position*.—Slightly asymmetrical.
*Transversal section shape*.—Circular.
*Maximum transversal section position*.—Central.
*Grooving*.—Weak.
*Groove distribution*.—Excluding apex.
*Number of grooves at the base*.—7–10.
*Groove distribution at the base*.—Regular.
*Apex shape in A position*.—Pointed.
*Apex shape in B position*.—Pointed.
*Mucron*.—Present.
*Base shape in A position*.—Pointed.
*Base shape in B position*.—Pointed.
*Suture conspicuousness*.—Weak.
*Suture curvature*.—Absent.

*Dimension*.—About 0.44 g to about 0.47 g, with longitudinal diameter from about 14.5 mm to about 16.5 mm and transversal diameter from about 7.0 mm to about 7.5 mm.

Flowering period: Late.

The typical and observed flowering period for a culture in the Umbrian region (Italy) ranges from about May 10th to about June 30th. The typical and observed ripening period for a culture in the Umbrian region (Italy) ranges from about November 20th to about December 15th.

Ripening period: Late.

Biological characteristics:

*Rooting attitude*.—High.

*Compatibility*.—Self-compatible.

*Ovarian abortion*.—Low (less than 10%).

Agronomic-technological characteristics:

*Production precocity*.—Precocious.

*Productivity*.—About 5,000 Kg/hectare to about 12,000 Kg/hectare in intensive plantations having 5'×3' spacing, depending on soil fertility and water availability.

*Production*.—Constant.

*Pulplstone ratio*.—7.5–8.5.

*Pulplstone detachment resistance*.—Easy.

*Drupe detachment resistance*.—Medium (251–500 g).

Resistance to abiotic factors:

*Cold*.—Medium-high.

*Water stress*.—Medium.

*Olea europaea L.* cv 'Don Carlo' resists temperatures from as low as about −8° C. to about −10° C. during the winter when plants are in vegetative rest time.

Resistance to parasites:

*Spilocaea oleagina*.—High.

*Pseudomonas savastanoi*.—High.

Qualitative parameters:

*Oleic acid*.—Higher than 75%.

*Polyphenol content*.—Medium-high.

*Organoleptic characteristics of the oil*.—Medium fruity — intense with slightly bitter aftertaste.

I claim:

1. A new and distinct selection of *Olea europaea* tree as shown and described herein.

* * * * *

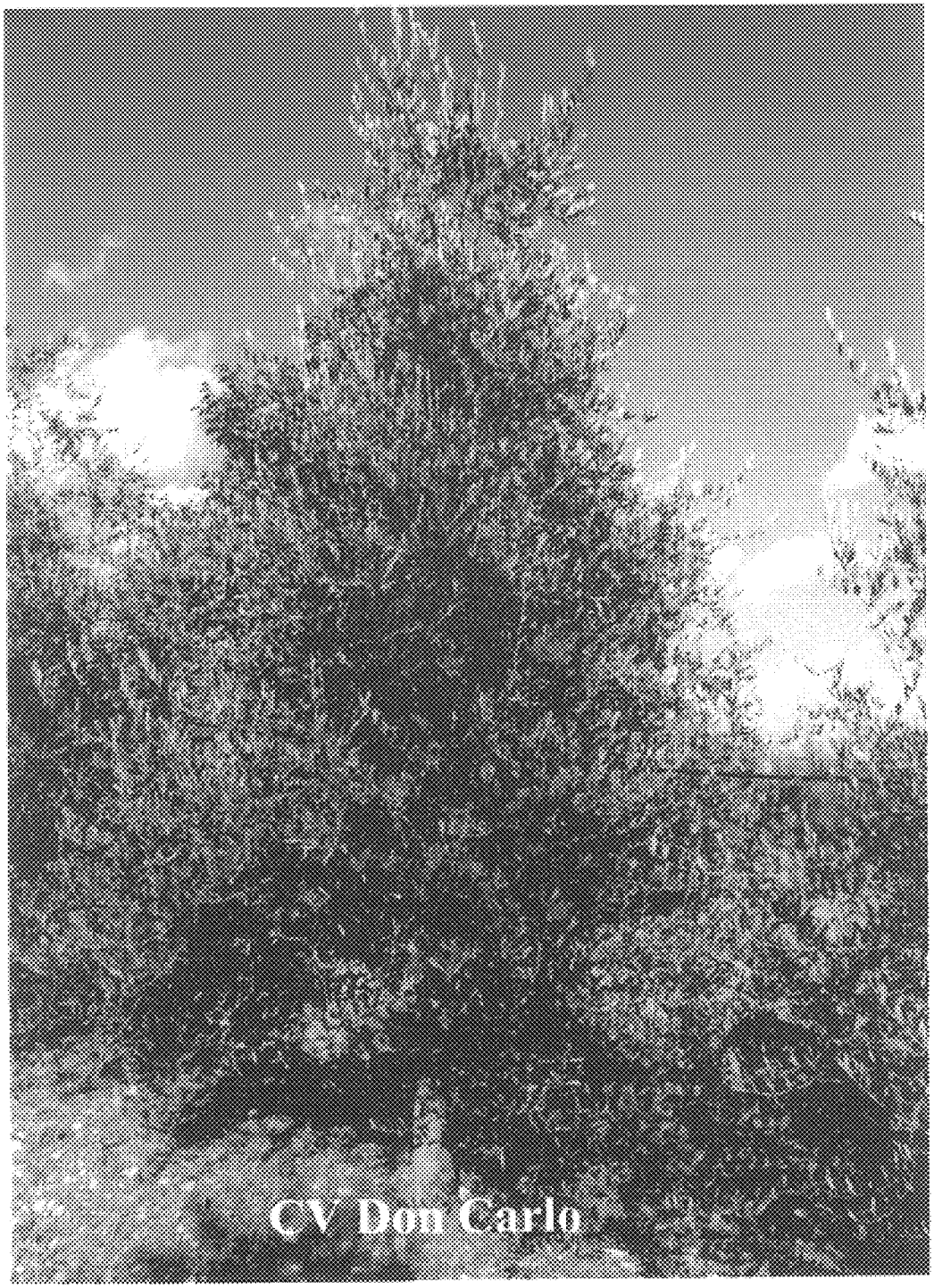
CV Don Carlo

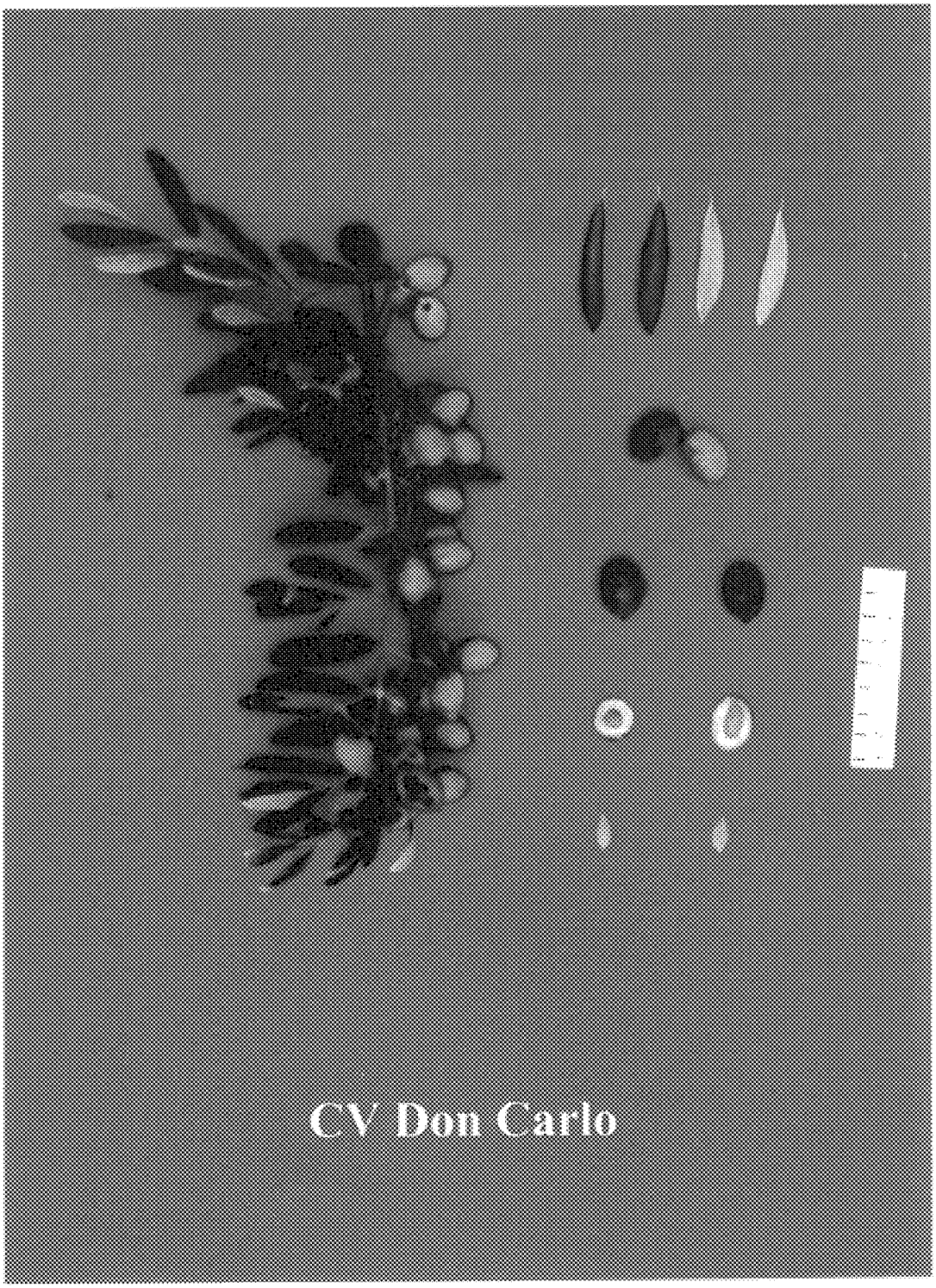
CV Don Carlo

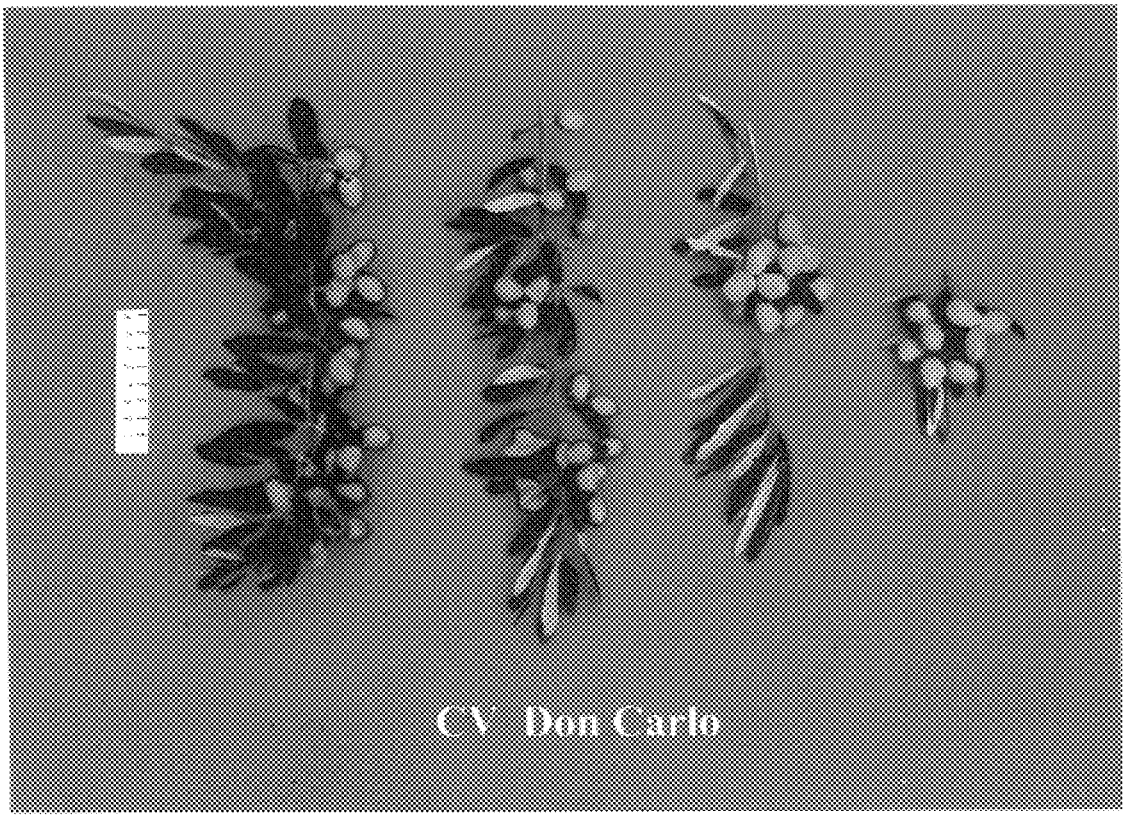
CV Don Carlo

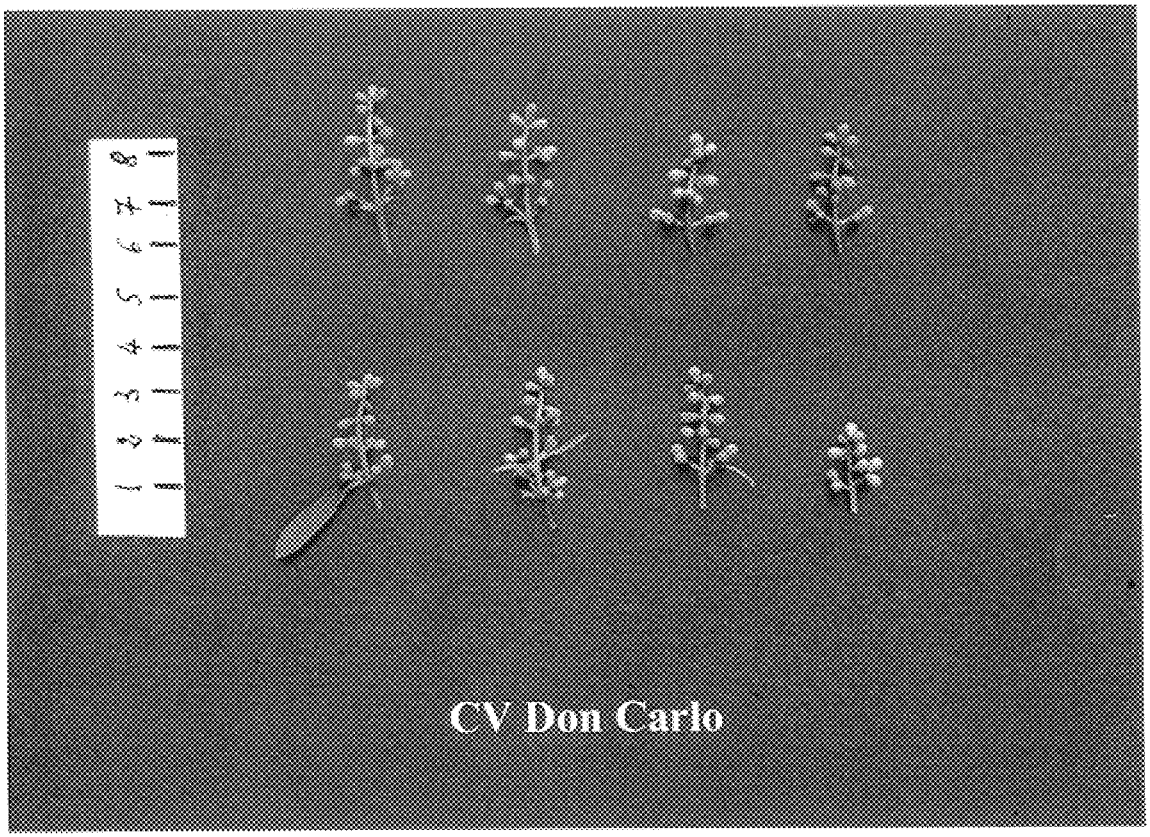
1 2 3 4 5 6 7 8
CV Don Carlo